United States Patent [19]

Wittemann

[11] 4,243,051
[45] Jan. 6, 1981

[54] DISPOSABLE ELECTRODE

[75] Inventor: Robert F. Wittemann, New Brunswick, N.J.

[73] Assignee: Johnson & Johnson, New Brunswick, N.J.

[21] Appl. No.: 1,501

[22] Filed: Jan. 8, 1979

[51] Int. Cl.³ .............................................. A61N 1/04
[52] U.S. Cl. ..................................... 128/798; 128/802
[58] Field of Search ............................... 128/639–641, 128/644, 303.13, 783, 798, 802, 803

[56] References Cited

U.S. PATENT DOCUMENTS

| | | | |
|---|---|---|---|
| 1,989,282 | 1/1935 | Kimble et al. | 128/798 |
| 3,426,746 | 2/1969 | Seamons, Jr. | 128/640 |
| 3,565,059 | 2/1971 | Hauser et al. | 128/640 |
| 4,008,721 | 2/1977 | Burton | 128/802 |
| 4,066,078 | 1/1978 | Berg | 128/641 |
| 4,141,366 | 2/1979 | Cross, Jr. et al. | 128/640 |

FOREIGN PATENT DOCUMENTS 2814061  10/1978  Fed. Rep. of Germany ...... 128/303.13

*Primary Examiner*—Lee S. Cohen
*Attorney, Agent, or Firm*—Audley A. Ciamporcero, Jr.

[57] ABSTRACT

A disposable electrode includes a fabric backing and a conductive mesh layer laminated thereto. A conductive polymer adhesive interfaces the conductive mesh with the skin of the patient. In order to promote uniform current density, connection to external apparatus occurs by means of a stranded wire which meets the mesh at a point and extends laterally therefrom along the electrode, intermediate the mesh and the adhesive.

2 Claims, 4 Drawing Figures

DISPOSABLE ELECTRODE

BACKGROUND OF THE INVENTION

This invention relates to disposable electrodes for providing electrical contact with the patient's skin, and more particularly to structural improvements in electrodes useful for post-operative and chronic electronic pain control.

CROSS REFERENCE TO RELATED APPLICATIONS

Reference may be had to the following concurrently filed copending applications:
- U.S. Ser. No. 1,503, L. Lazar et al, "Electrosurgical Grounding Pad" (Docket J&J 964)
- U.S. Ser. No. 1,502, W. D. Bailey, "Disposable Electrode" (Docket STM-20).

DISCLOSURE OF THE PRIOR ART

In U.S. Pat. No. 4,066,078 to Berg, issued Jan. 3, 1978 and entitled "Disposable Electrode," there is disclosed an electrode configuration utilizing electrically conductive adhesive materials of polymeric composition. In accordance with that disclosure, a conductive layer has disposed thereon a terminal for connection with an external apparatus. Polymer adhesive material having electrical conduction capability is provided as a substrate to the conductive layer. The adhesive material conforms to the patient's skin, in electrical as well as physical contact therewith, to disperse or collect electrical current or charge to or from the patient. A preferred embodiment disclosed therein utilizes a screen or mesh conductive sheet disposed within the polymeric substrate, further to provide uniform electrical characteristics for the entire electrode.

SUMMARY OF THE INVENTION

The present invention relates to adaptations of the type of electrode set forth in the above-described U.S. Pat. No. 4,066,078 to Berg, particularly concerning applications for transcutaneous electrical nerve stimulation such as post-operative and chronic pain control. In accordance with the principles of the present invention, an overlying non-conductive fabric layer, configured in accordance with the ultimate electrode shape, has laminated thereto a flexible conductive mesh. An external stimulating apparatus is electrically coupled to the conductive mesh by means of a stranded wire or cable which extends along the mesh and in electrical contact therewith. A tape member or other suitable means overlays the wire strands and holds them in physical and electrical contact with the mesh, also providing lateral tensile strength for the overall electrode. A substrate layer of electrically conductive polymer adhesive material coats the underside of the electrode, providing a full physical and electrical interface/contact between the mesh and the skin of the patient.

It is a feature of the present invention that the elongated wire portions provide superior current density characteristics over the entire electrode, thereby substantially promoting the desired electrical stimulation capacity. Further, substantial physical integrity is provided with respect to the entire electrode, thereby minimizing deleterious effects upon uniform current density characteristics, such as might result from stretching of the electrode during installation or adjustment thereof with respect to the patient.

BEST MODE FOR CARRYING OUT THE INVENTION

Basic features of electrodes for application to a patient's body, and particularly for purposes of transcutaneous nerve stimulation, include adequate flexibility or draping to facilitate contact over the contour of the patient's body, uniform current density over the desired area of stimulation, uniform adherence of the electrode to the patient's skin, and stable electrical characteristics for the duration of use or reuse of the electrode. Even in the case of a "one-shot" disposable electrode, in which no reuse is contemplated, it is important that the structural and electrical integrity of the electrode be maintained while the paper backer is stripped off in anticipation of application, and while the electrode is adjusted or readjusted for proper positioning on the patient.

Figure 1:
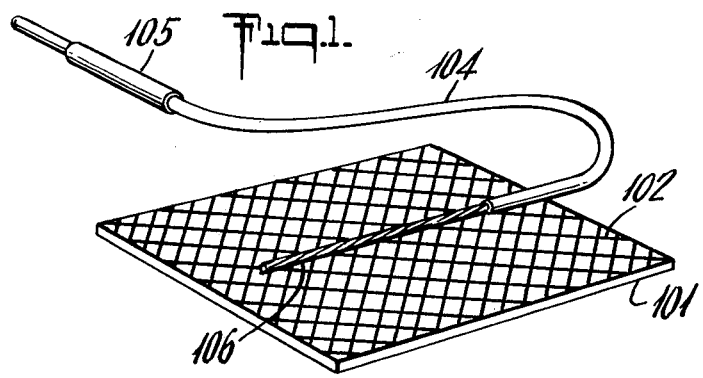
FIG. 1 shows an isometric view of a partially complete electrode embodying the principles of the present invention, viewed from the underside thereof, at the time of installation of a wire for interconnection with external apparatus.
Figure 2:
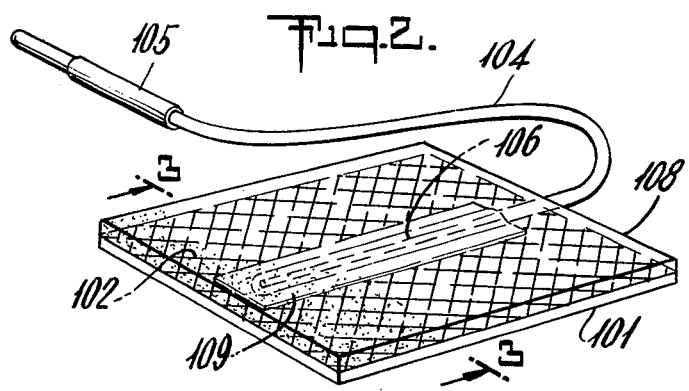
FIG. 2 shows a similar view of a portion of the same electrode, upon subsequent application of insulating reinforcement over the external connection wires.
Figure 3:
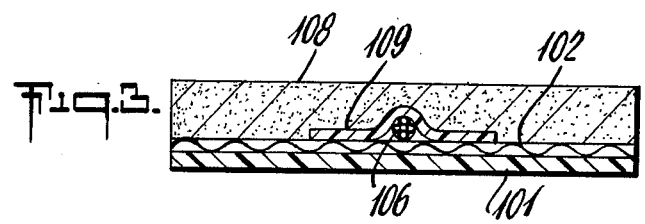
FIG. 3 shows a transverse cut-away of the FIG. 2 electrode, further including installation of a conductive substrate of polymer adhesive material.

The embodiment set forth in FIGS. 1-3 relates to improvements whereby such results may be obtained. With respect to basic electrode construction, reference may be had to the above-cited U.S. Pat. No. 4,066,078 to Berg or to a concurrently filed copending application of L. Lazar et al entitled "Electrosurgical Grounding Pad". The latter sets forth an electrode structure, and method of constructing the same, of a disposable electrode similar to the one disclosed in FIGS. 1-3 hereof.

The basic structure of the electrode of FIGS. 1, 2 and 3, as well as that set forth in the above referenced copending application of Lazar et al is that of a fabric (and/or foam) top, to which a conductive material is laminated, such as by means of an intermediate layer of foam. To the conductive material there is applied a substrate of polymeric adhesive gel which provides an electrically conductive, physically adherent interface between the laminated conductive layer of the electrode, and the skin of the patient. In FIGS. 1-3, a fabric layer 101, composed of a flexible material chosen for its draping properties, has laminated thereto a layer of flexible conductive material 102, also chosen for its draping properties. In a preferred embodiment, the fabric 101 is nylon tricot material, and layer 102 is a conductive material produced by sputtering aluminum onto a fabric base, for example the material commercially available from National Metallizers, Inc. under the trade designation "Delnet." In a preferred mode of construction, the fabric 101 and conductive layer 102 are flame laminated to one another by means of an intermediate layer of foam, for example the polyester foam commercially available as Tenneco Polyurethane foam FU10U.

In accordance with the principles of the present invention, prior to application of the polymeric adhesive conductive material 108 onto the conductive material 102, a wire 104 and plug 105 is provided for interconnection of the electrode with external apparatus, such as for example, a transcutaneous electrical nerve stimulation unit. In accordance with the principles of the present invention, the conductive aspects 106 of the wire or cable 104 constitute relatively fine stranded wires (e.g. 26 gauge silver or copper wire) which when affixed along the electrode, do not substantially affect the draping characteristics thereof, yet do not impair or limit unduly the current distribution capacity of the electrode. As shown most clearly in FIG. 1, the cable 104 extends along and in contact with the conductive surface 102, substantially along the length of the electrode.

Thereupon, a layer of insulating tape 109 is applied over the wire strands 106, maintaining them in physical and electrical contact with the conductive surface 102, but insulating the wires 106 from the subsequently applied polymeric adhesive material 108. Again, it is desirable that the tape material 109 be selected in part for its draping properties, such that while providing insulation between surface 102 and layer 108, and holding wire strands 106 in place, there results no detriment with respect to the ability of the overall electrode to conform to the shape of the patient's body. It will be appreciated that the presence of insulating tape member 109 provides not only the foregoing electrical properties, but furthermore provides reinforcement which substantially strengthens the electrode in the direction of the tape 109 and wire strands 106, to prevent stretch-type deformation which would adversely affect uniform current density over the surface 102.

When the wire strands 106 are in place as shown in FIG. 1, the insulating tape member 109 is supplied as shown in FIG. 2, and a substrate of conductive polymeric adhesive material 108 is applied such as shown in the cross-sectional view of FIG. 3. In a preferred embodiment, the adhesive material 108 is of a composition as set forth in the above-captioned Berg patent. For post-operative pain control applications, the polymer 108 is advantageously applied in a layer 25 mils thick.

An advantageous composition for the tape member 109, which is compatible with the adhesive material 108, is perforated, plasticized polyvinyl chloride tape currently available from Permacel under the trade designation "Derma-Clear." Such a tape not only meets the foregoing physical and electrical properties, but furthermore is sterilizable by radiation techniques, as is the entire electrode constructed in accordance with the foregoing.

Figure 4:
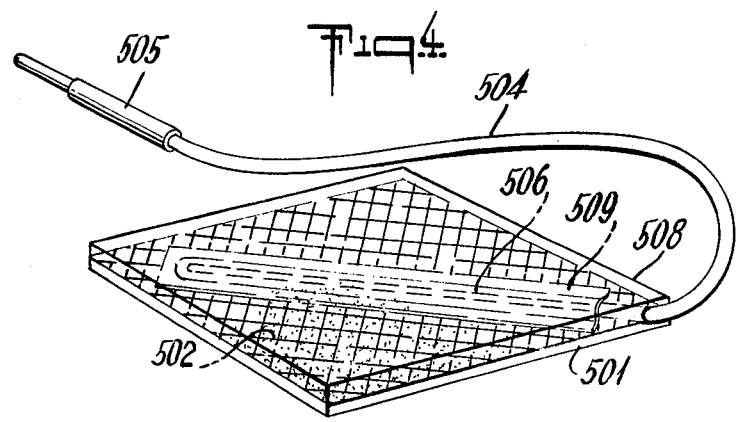
FIG. 4 shows an alternative embodiment of the principles of the present invention.

In an alternative form, shown in FIG. 4, the wire strands 506 associated with cable 504, plug 505 and overlying tape 509 are placed diagonally along the electrode 501, 502, 508.

It will be understood that the foregoing sets forth preferred embodiments of the principles of the present invention, but that numerous alternatives will occur to those of ordinary skill in the art without departure from the spirit or scope of the present invention.

I claim:

1. A transcutaneous electrode providing electrical contact with a patient's skin, having substantial uniformity of current density and resistance to physical deformation comprising:
   (a) a conductive member having upper and lower surfaces and generally defining the configuration of said electrode;
   (b) an electrically conductive adhesive material, electrically and physically connected to and covering the lower surface of said conductive member, for interfacing said conductive member with the patient's skin;
   (c) electrical connection means for physically and electrically coupling said conductive member with an external electrical apparatus, said connection means including an electrical conductor joining said conductive member at a contact point along a side of said conductive member, thence extending away from said point substantially across the lower surface of said conductive member, said electrical conductor being in electrically conductive relation with said conductive member substantially across said lower surface; and
   (d) an electrically insulating tape reinforcing means overlaying the full length of said electrical conductor and simultaneously being bonded to said lower surface.

2. An electrode as described in claim 1 wherein said conductive member comprises an electrically conductive mesh material, said electrical conductor is wire, and said electrode further comprises a top overlayment insulator pad laminated onto and substantially co-extensive with said upper surface.

* * * * *